(12) United States Patent
Daley

(10) Patent No.: US 10,471,187 B2
(45) Date of Patent: Nov. 12, 2019

(54) APPARATUS AND METHOD FOR REMOVING DEBRIS FROM AN ORIFICE

(71) Applicant: Daley Solutions, LLC, Summertown, TN (US)

(72) Inventor: Todd R. Daley, Summertown, TN (US)

( * ) Notice: Subject to any disclaimer, the term of this patent is extended or adjusted under 35 U.S.C. 154(b) by 392 days.

(21) Appl. No.: 15/290,924

(22) Filed: Oct. 11, 2016

(65) Prior Publication Data

US 2017/0224886 A1    Aug. 10, 2017

Related U.S. Application Data

(60) Provisional application No. 62/292,911, filed on Feb. 9, 2016.

(51) Int. Cl.
| | |
|---|---|
| *A61M 5/00* | (2006.01) |
| *A61M 1/00* | (2006.01) |
| *A61M 25/00* | (2006.01) |
| *A61M 31/00* | (2006.01) |
| *A61M 25/16* | (2006.01) |
| *A61M 39/02* | (2006.01) |
| *A61M 27/00* | (2006.01) |

(52) U.S. Cl.
CPC ... *A61M 1/0039* (2013.01); *A61M 2210/0662* (2013.01)

(58) Field of Classification Search
CPC ........ A61M 5/00; A61M 25/00; A61M 31/00; A61M 25/16; A61M 39/02; A61M 27/00; A61K 9/02
See application file for complete search history.

(56) References Cited

U.S. PATENT DOCUMENTS 9,114,202 B1 *   8/2015   Huttner ............... A61M 1/0039

* cited by examiner

*Primary Examiner* — Tatyana Zalukaeva
*Assistant Examiner* — Ilya Y Treyger
(74) *Attorney, Agent, or Firm* — Bradley Arant Boult Cummings; Timothy L. Capria

(57) ABSTRACT

An apparatus for removing debris from an orifice of a subject includes a nozzle, a body and a base. The apparatus is configured such that it can be interoperably received on a vacuum hose of varying makes and models of household vacuums and wet/dry vacuums. The apparatus has a body cavity configured to be in gaseous communication with the vacuum hose and the orifice of the subject when suction is provided by the vacuum cleaner and the nozzle is inserted into the orifice of the subject. The orifice may be a human ear. A method of removing debris from an orifice is also described herein. The apparatus and method of the present disclosure, among other things, safely and effectively remove debris from the office without causing damage to the office and the surrounding tissue.

20 Claims, 5 Drawing Sheets

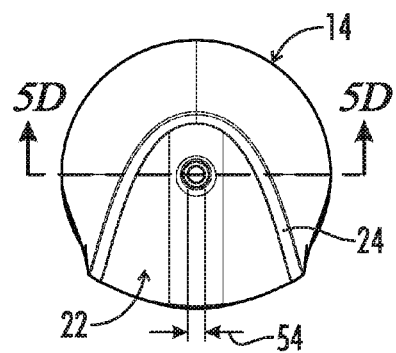
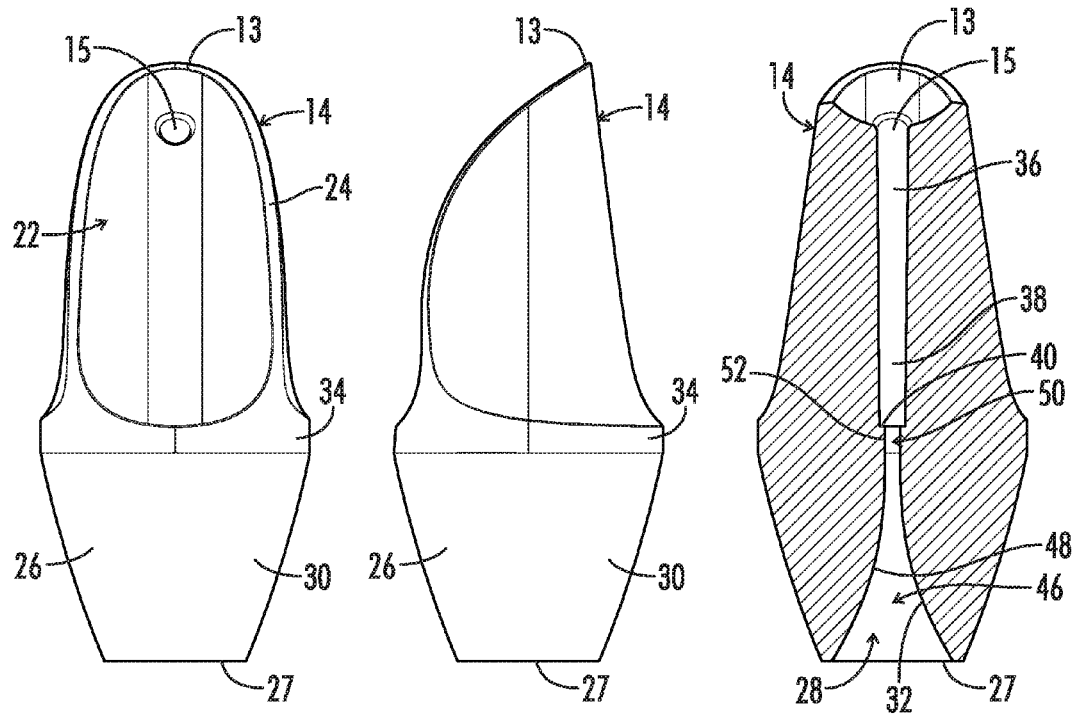
FIG. 5A
FIG. 5B  FIG. 5C  FIG. 5D

APPARATUS AND METHOD FOR REMOVING DEBRIS FROM AN ORIFICE

This is a Non-Provisional patent application filed for an invention by Todd R. Daley, a citizen of the United States, residing in Summertown, Tenn., for the disclosure of an "Apparatus and Method for Removing Debris from an Orifice." This application claims priority benefit of U.S. Provisional Patent Application No. 62/292,911, entitled "APPARATUS FOR REMOVING DEBRIS FROM AN EAR" which is hereby incorporated by reference in its entirety.

FIELD OF DISCLOSURE

The present disclosure relates generally to an apparatus for removing debris from an orifice, such as a human ear. The present disclosure also relates to a method of removing debris from an orifice.

BACKGROUND OF THE DISCLOSURE

Ear cleanliness and dryness are paramount for optimum ear and sinus health. Many individuals experience discomfort caused by a buildup of earwax, ear mucus and excess ear liquid, as well as any other native or foreign irritants that are in or around the ear canal. These individuals would benefit from an apparatus to remove earwax, ear mucus and excess ear liquid.

Known solutions for cleaning the ear canal and removing debris from the ear canal, such as cotton swabs or ear scoops, are inadequate. For example, cotton swabs and ear scoops can compact or push ear mucus and other debris further into the ear, leading to a possible ear infection and other irritation in and around the ear of the subject. Moreover, cotton swabs risk becoming lodged in the ear of a subject, requiring medical intervention to remove. Thus, a need exists for an apparatus that is safe and effective for cleaning an ear of a subject and removing debris from the ear without scraping or otherwise potentially damaging the ear.

BRIEF SUMMARY OF THE DISCLOSURE

Advantageously, the apparatus of the present disclosure provides a user with a safe and effective method of clearing material from an orifice of a subject, such as an ear canal. The apparatus of the present disclosure can attach to a vacuum, such as a household vacuum cleaner or a wet/dry vacuum, to utilize the suction of the vacuum to remove debris from the ear of a subject. The apparatus of the present disclosure can also be used to remove debris from other orifices, such as a nose.

An apparatus for removing debris from an orifice is described herein. The apparatus comprises a body having a base end and a nozzle end. The body includes a body cavity defined within the body. A base disposed on the base end is configured to receive or be received on a vacuum cleaner hose. The base tapers inwardly toward the base end. The base is configured to be received on a vacuum cleaner hose. The body comprises a nozzle disposed on the nozzle end. The nozzle includes a nozzle interior in gaseous communication with the body cavity. The nozzle is configured to be received in an ear or other orifice of a subject, such as an animal or a human.

In an embodiment of the apparatus, the body has a first recess defined by an outer lip. The body comprises a second recess defined by the outer lip. The first recess and the second recess are each configured to receive one or more fingers of a user. The body includes an integrally formed ring disposed between each of the first recess and the base, and the second recess and the base. The body comprises a body cavity which includes a nozzle dock. The nozzle is configured to friction fit within the body cavity and to be removable from the body cavity. In an embodiment, the body includes a nozzle stop configured to prevent the nozzle from being inserted past the nozzle stop when the nozzle is inserted into the body cavity.

In an embodiment of the apparatus, the base includes a base aperture and a base chamber. The base chamber is in gaseous communication with the body cavity and the base aperture. The base chamber has an inwardly tapering profile toward the nozzle end. The inwardly tapering profile may be funnel-shaped.

Another embodiment is a method of removing debris from an orifice, such as a human ear, of a subject. The method includes providing an apparatus that comprises a body comprising a base end and a nozzle end. The body includes a body cavity defined within the body. The body includes a base disposed on the base end. The base is configured to receive or to be received on a vacuum cleaner hose. A nozzle disposed on the nozzle end includes a nozzle interior in gaseous communication with the body cavity. The method comprises attaching the base to the vacuum hose so that the interior chamber is in gaseous communication with the vacuum hose, and inserting the nozzle into the orifice of the subject. The method includes providing suction to the vacuum cleaner hose. The vacuum hose may be part of, or provided on, a house vacuum or a wet/dry vacuum. The subject may perform the removing or another person may perform the removing. The attaching of the base to the hose forms a seal between the vacuum hose and the base when the suction is provided. The nozzle is removable from the body when the method is completed.

BRIEF DESCRIPTION OF THE DRAWINGS

FIG. 5A is a top plan view of the body of FIG. 4.

FIG. 5B is front elevational view of the body of FIG. 4.

FIG. 5C is a right side elevational view of the body of FIG. 4.

FIG. 5D is a cross-sectional view of the body of FIG. 4 taken along the line 5D-5D in FIG. 5A.

DETAILED DESCRIPTION OF THE DISCLOSURE

Figure 1:
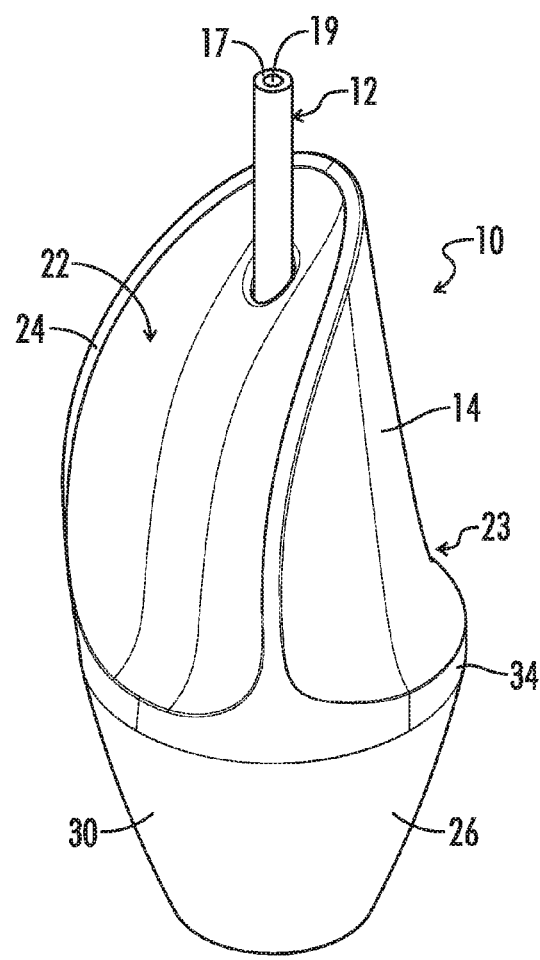
FIG. 1 is a front perspective view of an embodiment of the apparatus for removing debris from an orifice, the view illustrating a removable nozzle inserted into the body of the apparatus.
Figure 2:
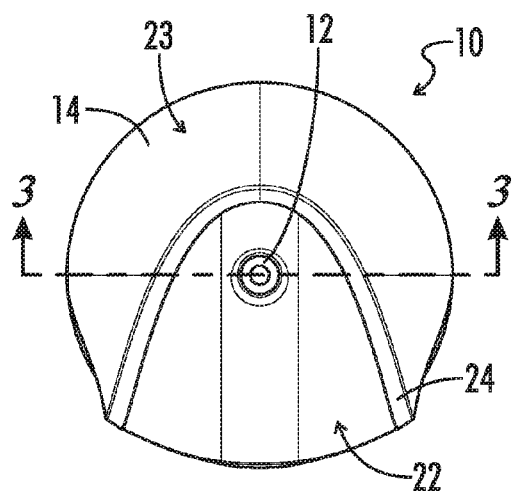
FIG. 2 is a top plan view of the body and the removable nozzle of FIG. 1.
Figure 3:
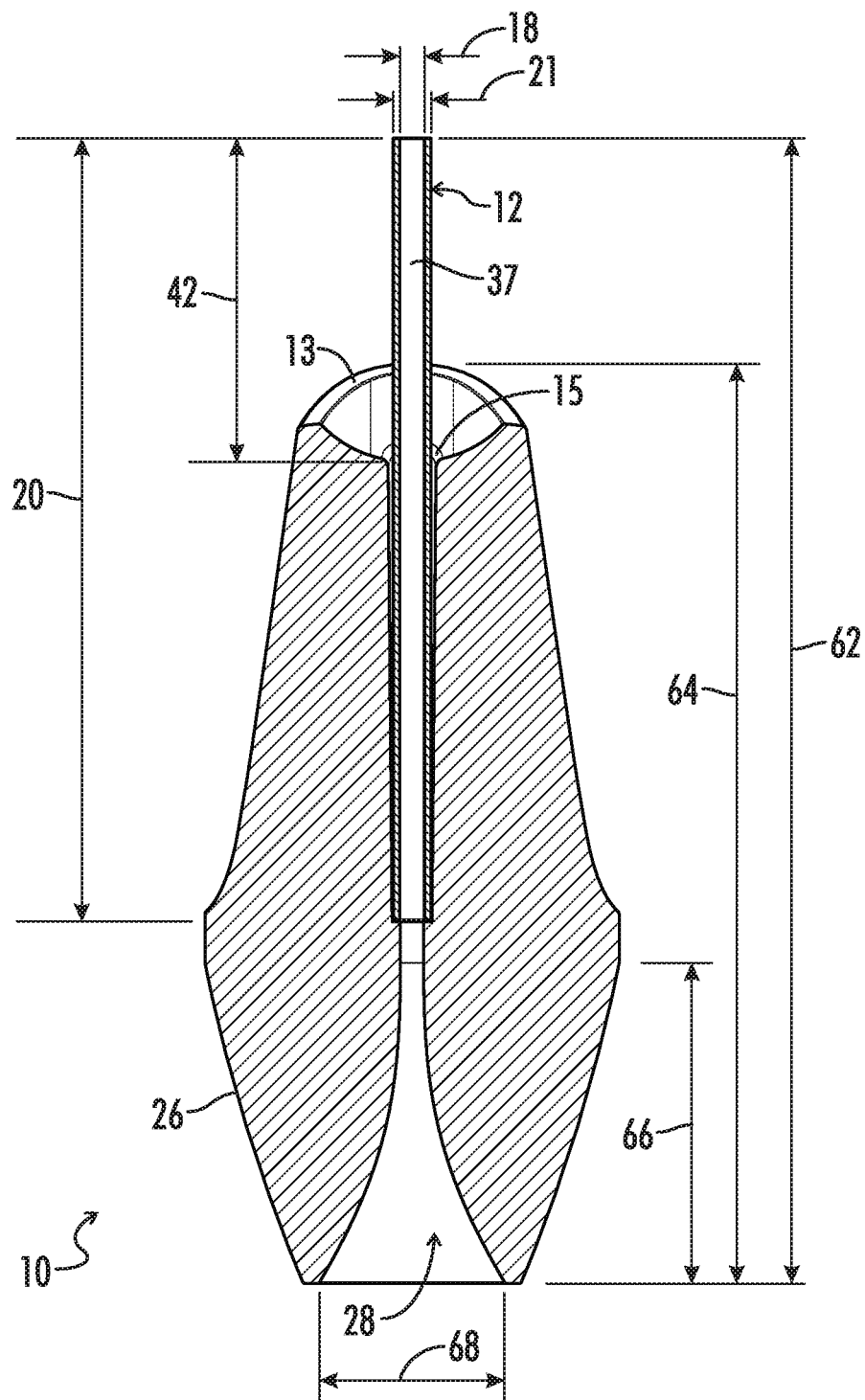
FIG. 3 is a cross-sectional view of the body and the removable nozzle of FIG. 1 taken along the line 3-3 in FIG. 2.
Figure 4:
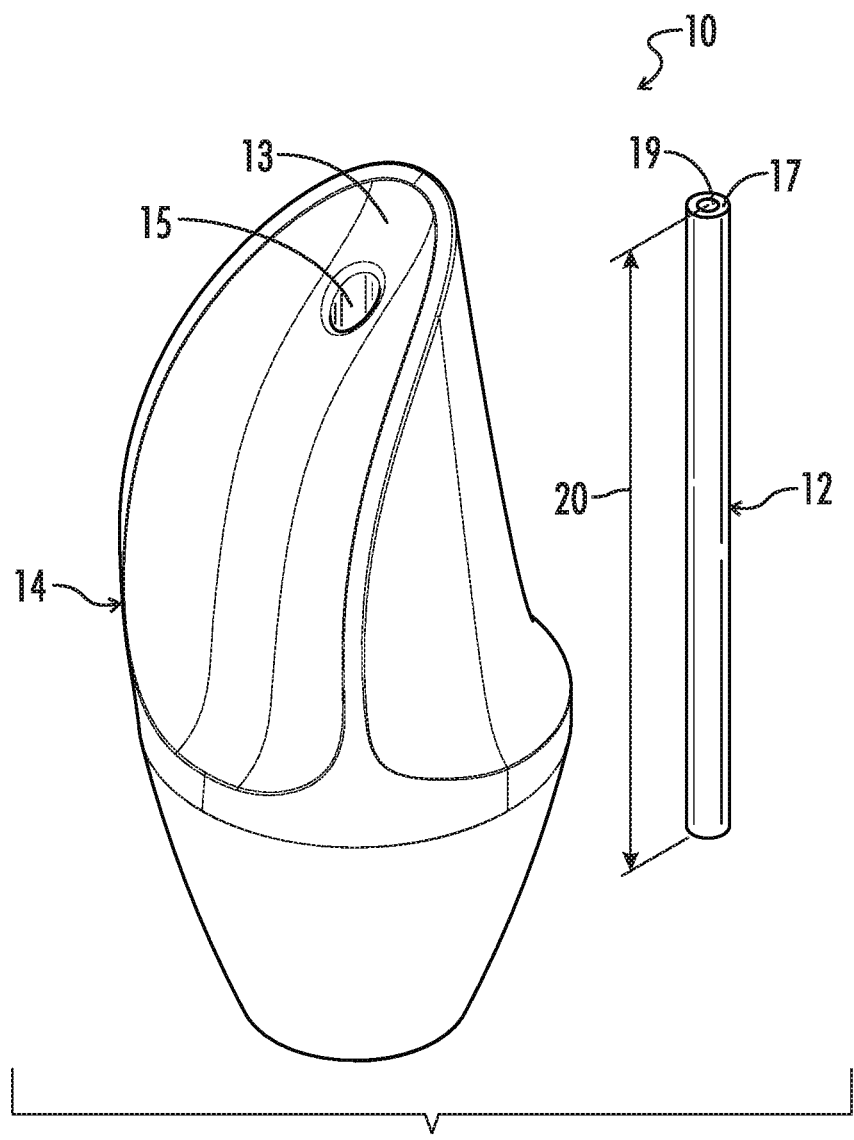
FIG. 4 is a front perspective view of the body and the nozzle of the apparatus of FIG. 1 with the nozzle removed from the body of the apparatus.

While the making and using of various embodiments of the present invention are discussed in detail below, it should be appreciated that the present invention provides many applicable inventive concepts that is embodied in a wide variety of specific contexts. The specific embodiments discussed herein are merely illustrative of specific ways to make and use the invention and do not delimit the scope of the invention.

As shown in FIGS. 1-4 and 5A-5D, an embodiment of the apparatus 10 for removing orifice debris includes a body 14 and a nozzle 12. The nozzle 12 has a nozzle tip 17 defined by a nozzle aperture 19. In an embodiment, the body 14 has a body aperture 15 formed at a nozzle end 13. The body aperture 15 is configured to receive the nozzle 12. The body 14, the nozzle 12, or both the body 14 and the nozzle 12 may be constructed of metal, such as stainless steel, or polymers such as polyethylene, polypropylene, polystyrene, polyester, polycarbonate, polyvinyl chloride, polyethersulfone, polyacrylate, hydrogen, polysulfone, polyetheretherketone, thermoplastic elastomers, thermoplastic polyurethanes, silicone, poly-p-xylylene, fluoropolymers, and combinations thereof. In an embodiment, the body 14 may be constructed of a compressibly resilient material, such as silicone, to assist a user in easily grasping, holding and controlling the apparatus 10. In the illustrated embodiment, the body 14 tapers inwardly towards the nozzle end 13. In preferred embodiments, the apparatus 10 is provided in a sterile configuration. The nozzle 12 may be disposable after each use.

The nozzle 12 has a nozzle interior 37. The nozzle 12 friction fits within the body aperture 15 and is removable therefrom. The nozzle 12 may also be integrally formed with the body 14. Advantageously, in embodiments where the nozzle 12 is removable, a user may remove the nozzle 12 to, for example, clean the nozzle 12, clean the nozzle interior 37, clean the body 14, replace the nozzle 12 with a replacement nozzle 12, and replace the nozzle 12 with a differently sized nozzle 12. The nozzle 12 has a nozzle inner diameter 18, a nozzle outer diameter 21 and a nozzle length 20. One or more of the nozzle inner diameter 18, the nozzle outer diameter 21 and the nozzle length 20 may have a dimension that can be selected to be configured to be received in different orifices of a variety of populations of users. For example, the nozzle diameter 18 and the nozzle length 20 may be larger in size for adult subjects and smaller in size for child subjects. In another example, the nozzle diameter 18 and the nozzle length 20 may vary as to be configured to be received in a nasal canal of a user or an ear canal of a user. The nozzle 12 may have a cylindrical profile or may have a profile shaped as to be configured to be received in an orifice, such as an ear, in a subject.

In an illustrated embodiment, the body 14 includes a first recess 22 defined by an outer lip 24. The nozzle aperture 15 may be disposed within the first recess 22. The first recess 22 enables a user to firmly grip and precisely control the apparatus 10. A firm grip and precise control are important because the apparatus 10 is used in sensitive areas of a subject's body. The first recess 22 may be oblong and curved such that it is configured to ergonomically receive a finger of a user, such as an index finger, a middle finger, or a ring finger.

The body 14 may include a second recess 23. The second recess 23 may be opposite the first recess 22. The second recess 23 may be configured to receive a finger of a user, such as a thumb. The second recess 23 may contribute to increased control and grip of the apparatus 10 when the apparatus 10 is in use. In an embodiment, the first recess 22 and the second recess 23 are integrally formed in the body 14.

Figure 6:
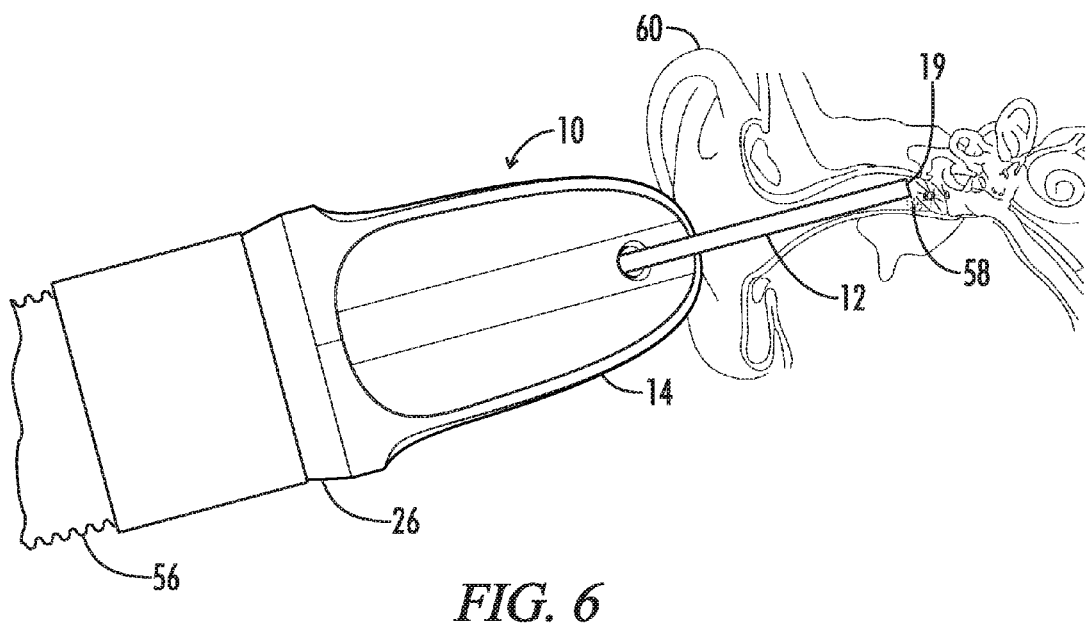
FIG. 6 is a side view of an embodiment of the apparatus for removing debris entering an ear of a subject.

In an embodiment, the body 14 is configured such that when the nozzle 12 is inserted into an orifice of a subject, as shown in FIG. 6, the body 14 prevents the nozzle 12 from being inserted further into the orifice as the body 14 comes into contact with the subject. For example, the outer lip 24 may be configured to contact a subject when the nozzle 12 is inserted a predetermined distance into an orifice, thus stopping further insertion of the nozzle 12. The stoppage of the nozzle 12 may prevent a user from inserting the nozzle 12 so far into an orifice as to damage the surrounding tissue of the subject.

In an illustrated embodiment, a base 26 is disposed on the body 14. The base 26 may be integrally formed with body 14 and located opposite the nozzle end 13. The base 26 includes a base aperture 28 positioned at a base end 27 that is opposite the nozzle end 13. The base 26 may be configured to be received on, or to receive, a vacuum hose 56, as shown in FIG. 6. The base 26 has an external base surface 30. The external base surface 30 may be cylindrical in shape. In the illustrated embodiment, the base surface 30 tapers inwardly toward the base end 27. The inward tapering of the external base surface 30 enables the base 26 to be received in and friction fit with vacuum hoses of varying diameters such that the apparatus 10 is interoperable with the hoses of various makes and models of vacuums, including household vacuums and wet/dry vacuums. In an alternate embodiment, the base 26 may have an internal base surface 32 that tapers outwardly toward the base end 27 such that the base aperture 28 is configured to receive various vacuum hoses. Examples of household vacuum cleaners and wet/dry vacuum cleaners with which apparatus 10 may be interoperable include upright vacuums, bag and bagless vacuums, canister vacuums and handheld vacuums.

In the illustrated embodiment, the body 14 has a ring 34 circumferentially extending around the body 14. The ring 34 is positioned between recesses 22 and 23 and the base 26. The ring 34 has a diameter at least as great as the largest diameter of the tapered outer surface 30. In embodiments where the body 14 is configured to be received in a vacuum hose, the ring 34 may prevent the body 14 from being undesirably sucked into the hose during use. The ring 34 may also function as a point of contact between one or more fingers of a user and body 14. The body 14, the base 26, the ring 34, and/or the outer lip 24 may be integrally formed as one piece.

As shown in the illustrated embodiment, the apparatus 10 includes the body 14 having the body aperture 15 positioned towards the nozzle end 13 of the body 14. The body aperture 15 is in gaseous communication with a body cavity 36. The body cavity 36 extends from the body aperture 15 to the base aperture 28. The body cavity 36 is configured to receive the nozzle 12 in a nozzle dock 38. The nozzle dock 38 is configured to securely and removably receive the nozzle 12. The nozzle dock 38 tapers inwardly toward the base end 27. The cavity 36 may include a nozzle stop 40 positioned away from the nozzle end 13 and toward the base end 27. The nozzle stop 40 is configured to prevent the nozzle 12 from being inserted past the nozzle dock 38 in a direction. In the illustrated embodiment, the nozzle stop 40 is formed of a narrowed section of the cavity 36 that is configured to stop the nozzle 12 while allowing gaseous communication through the cavity 36 from the nozzle end 13 to the base end 27. The nozzle stop 40 stops the nozzle 12 such that a predetermined length 42 of the nozzle 12 protrudes from the body aperture 15. Advantageously, in conjunction with the nozzle stop 40, the predetermined length 42 of nozzle 12 provides a user with a safe and effective length of nozzle to insert into the user's orifice, reducing the risk of tissue damage and making the apparatus 10 safe and user-friendly.

A base chamber 46 may formed in, and in gaseous communication with, the body cavity 36. The base chamber 46 may be positioned at the base end 27. The base chamber 46 may have a tapered profile 48, such as a funnel-shape, that inwardly tapers from the base aperture 28 toward the nozzle stop 40. An intermediate cavity 50 may be disposed between the base chamber 46 and the nozzle stop 40. The intermediate cavity 50 may have a cylindrical profile such that it has a cylindrical cavity sidewall 52. The intermediate cavity 50 has an intermediate cavity diameter 54 (see FIG. 5A). Advantageously, the tapered profile 48 and the intermediate cavity diameter 54 may be selected to control the volume and velocity of air movement from the nozzle 12 to the base aperture 28. Based on this, the speed and volume of air movement at the nozzle tip 17 may be modulated such that the speed and volume are sufficient to remove debris from an orifice proximate to the nozzle tip 17 while not damaging tissue of the subject.

In the illustrated embodiment, the apparatus 10 has an apparatus length 62 of between 2 inches and 5 inches, (e.g., about 3.75 inches). The nozzle 12 has a nozzle length 20 of between 0.5 inch and 5 inches, (e.g., about 3 inches). The nozzle aperture 19 includes an inner nozzle diameter 18 of from 0.025 inch to 0.25 inch, (e.g., 0.09375 inch). The nozzle 12 includes an outer nozzle diameter 21 of from 0.05 inch to 0.5 inch, (e.g., about 0.15625 inch). The inner nozzle diameter 18 may be selected to proportionally modulate the amount of airflow provided through the nozzle 12. The body 14 includes a body length 64 of from 0.5 inch to 5 inches, (e.g., about 1.25 inches). The base 26 includes a base length 66 of from 0.5 inch to 3 inches, (e.g., about 1.25 inches). The base aperture 28 includes a base aperture diameter 68 of from 0.5 inch to 3 inches, (e.g., about 1 inch). The foregoing are examples of dimensions in certain embodiments. The dimensions of the components of the apparatus may be varied based on, for example, the age, size and gender of the subject.

As shown in FIG. 6, an embodiment of the apparatus 10 is operably attached to a vacuum hose 56 to provide suction from the vacuum hose 56 through the body cavity 36 (shown in FIG. 5D) and the nozzle 12 to remove one or more debris 58 from an orifice 60 of a subject, such as a human ear. The debris 58 is removed from the orifice 60 by the suction through the nozzle 12 and through the vacuum hose 56. In particular, the suction moves the debris 58 through the nozzle aperture 19 and into the body cavity 36 (shown in FIG. 5D). In particular, the suction allows the debris 58 to be carried from the ear 60 through the nozzle aperture 19 and the nozzle 12 into the body 14, the base 26 and the hose 56.

When the base 26 of the apparatus 10 is received in the vacuum hose 56, the external base surface 30 (shown in FIGS. 5B and 5C) forms a seal with the vacuum hose 56, such that air does not, or substantially does not, pass into the vacuum hose 56 without passing through the nozzle tip 17. The shape of base surface 30 contributes to the ability of the apparatus 10 to be interoperable with the hoses of different types of vacuums.

A method of removing debris from an orifice, such as a human ear, of a subject is disclosed. The method may include providing an apparatus that comprises a body comprising a base end and a nozzle end, the body including a body cavity defined by the body. The body may include a base disposed on the base end, the base configured to receive or be received on a vacuum cleaner hose, and a nozzle disposed on the nozzle end, the nozzle including a nozzle interior in gaseous communication with the body cavity. The method may comprise attaching the base to the vacuum hose so that the interior chamber is in gaseous communication with the vacuum hose, and inserting the nozzle into the orifice of the subject. The method may include providing suction to the vacuum cleaner hose. The vacuum hose may be part of, or provided on, a house vacuum or a wet/dry vacuum. The subject may be performing the removing. The attaching of the base to the hose may form a seal between the vacuum hose and the base when the suction is provided. The nozzle may be removable from the body.

In an embodiment, the method removes cerumen, or earwax, from an ear. The present method may be used to treat excessive cerumen from an ear in a subject. The present method may treat symptoms caused by excessive earwax build up, such as sudden or partial hearing loss, tinnitus or an earache. The present method may be used to remove impacted ear wax or an earwax blockage from a subject.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

What is claimed is:

1. An apparatus for removing debris from an orifice, comprising:
   a body comprising a base end and a nozzle end, the body including
   a body cavity defined within the body,
   a base disposed on the base end, the base including a base aperture and a base chamber, the base chamber in gaseous communication with the body cavity and the base aperture, wherein the base chamber has an inwardly tapering profile toward the nozzle end, and wherein the base is configured to receive or to be received on a vacuum cleaner hose, and
   a nozzle removably disposed on the nozzle end, the nozzle including a nozzle interior in gaseous communication with the body cavity, the nozzle configured to have a peripheral size and a length to enter into an orifice.

2. The apparatus of claim 1, wherein the base tapers inwardly toward the base end, and the base is configured to be received on a vacuum cleaner hose.

3. The apparatus of claim 1, wherein the nozzle is configured to be received in an ear of a subject.

4. The apparatus of claim 1, wherein the body has a first recess defined by an outer lip.

5. The apparatus of claim 4, wherein the body has a second recess defined by an outer lip.

6. The apparatus of claim 5, wherein the first recess and the second recess each are configured to receive one or more fingers of a user.

7. The apparatus of claim 5, wherein the body includes an integrally formed ring disposed between each of the first recess and the base, and the second recess and the base.

8. The apparatus of claim 1, wherein body cavity includes a nozzle dock.

9. The apparatus of claim 1, wherein the nozzle is configured to be removable from the body cavity.

10. The apparatus of claim 9, wherein the nozzle is configured to friction fit within the body cavity.

11. The apparatus of claim 1, wherein the body includes a nozzle stop configured to prevent the nozzle from being inserted past the nozzle stop when the nozzle is inserted into the body cavity.

12. The apparatus of claim 1, wherein the inwardly tapering profile is funnel-shaped.

13. A method of removing ear debris from an orifice of a subject, comprising
providing an apparatus, comprising:
a body comprising a base end and a nozzle end, the body including
a body cavity defined by the body,
a base disposed on the base end, the base including a base aperture and a base chamber, the base chamber in gaseous communication with the body cavity and the base aperture, wherein the base chamber has an inwardly tapering profile toward the nozzle end, and wherein the base is configured to receive or be received on a vacuum cleaner hose, and
a nozzle removably disposed on the nozzle end, the nozzle including a nozzle interior in gaseous communication with the body cavity;
attaching the base to the vacuum hose so that the interior chamber is in gaseous communication with the vacuum hose;
inserting the nozzle into the orifice of the subject; and
providing suction to the vacuum cleaner hose.

14. The method of claim 13, wherein the orifice is a human ear.

15. The method of claim 13, wherein the vacuum hose is provided on a household vacuum or a wet/dry vacuum.

16. The method of claim 13, wherein the attaching includes inserting the base into the vacuum hose such that a seal is formed between the vacuum hose and the base when the suction is provided.

17. The method of claim 13, wherein the nozzle is removable from the body.

18. The method of claim 13, wherein the body includes a first recess and a second recess, wherein each of the first recess and the second recess are configured to receive at least one finger of a user.

19. The method of claim 13, wherein the subject is performing the removing.

20. The method of claim 13, wherein the inwardly tapering profile of the base chamber is funnel-shaped.

* * * * *